(12) United States Patent
Schuessler et al.

(10) Patent No.: US 9,486,308 B2
(45) Date of Patent: Nov. 8, 2016

(54) METHOD OF MAKING A REINFORCED PROSTHETIC IMPLANT WITH FLEXIBLE SHELL

(71) Applicant: ALLERGAN, INC., Irvine, CA (US)

(72) Inventors: David J. Schuessler, Ventura, CA (US); Ahmet Tezel, Fort Worth, TX (US)

(73) Assignee: ALLERGAN, INC., Irvine, CA (US)

( * ) Notice: Subject to any disclaimer, the term of this patent is extended or adjusted under 35 U.S.C. 154(b) by 385 days.

(21) Appl. No.: 14/088,163

(22) Filed: Nov. 22, 2013

(65) Prior Publication Data

US 2014/0077411 A1    Mar. 20, 2014

Related U.S. Application Data

(62) Division of application No. 12/853,003, filed on Aug. 9, 2010, now abandoned.

(60) Provisional application No. 61/234,751, filed on Aug. 18, 2009.

(51) Int. Cl.
| | |
|---|---|
| B29C 41/04 | (2006.01) |
| A61F 2/12 | (2006.01) |
| B29C 41/22 | (2006.01) |
| A61L 27/18 | (2006.01) |
| A61L 27/50 | (2006.01) |

(52) U.S. Cl.
CPC ............... *A61F 2/12* (2013.01); *A61L 27/18* (2013.01); *A61L 27/50* (2013.01); *B29C 41/04* (2013.01); *B29C 41/22* (2013.01); *A61L 2430/04* (2013.01)

(58) Field of Classification Search
None
See application file for complete search history.

(56) References Cited

U.S. PATENT DOCUMENTS

| | | | |
|---|---|---|---|
| 3,366,975 | A | 2/1968 | Pangman |
| 4,455,691 | A | 6/1984 | Van Aken Redinger |
| 4,592,755 | A | 6/1986 | Penton |
| 4,650,487 | A | 3/1987 | Chaglassian |
| 4,773,909 | A | 9/1988 | Chaglassian |
| 4,790,848 | A | 12/1988 | Cronin |
| 4,823,815 | A | 4/1989 | Watson et al. |
| 5,447,535 | A * | 9/1995 | Muller ............. A61F 2/12 623/8 |
| 5,480,430 | A * | 1/1996 | Carlisle ............ A61F 2/12 623/7 |

(Continued)

FOREIGN PATENT DOCUMENTS

| | | |
|---|---|---|
| EP | 0029292 B1 | 5/1981 |
| EP | 0030838 A1 | 6/1981 |

*Primary Examiner* — Edmund Lee
(74) *Attorney, Agent, or Firm* — Linda Allyson Nassif

(57) ABSTRACT

A fluid-filled soft prosthetic implant having a shell with a reinforced shell wall. The soft prosthetic implant may be for breast reconstruction or augmentation, or to restore the normal appearance of soft tissue in the buttocks, chin, calf, etc. The implants may be reinforced using several methods: reinforcement of the shell wall, non-homogeneous gel-filling, or both. At least a portion of the perimeter region desirably has a shell wall thickness greater than the average shell wall thickness of either the anterior face or the posterior face. The added material at the perimeter region strengthens that area in which a large percentage of implant ruptures occur. The reinforced perimeter also helps prevent the implant from collapsing or folding, which can cause undesirable rippling or wrinkling visible through the patient's skin. The remainder of the shell will desirably have a nominal wall thickness to retain the overall softness and supple feel of the implant. The implant shell may be filled with gels of different gel cohesiveness to counterbalance any reinforced area or to provide added reinforcement.

4 Claims, 2 Drawing Sheets

(56) References Cited

U.S. PATENT DOCUMENTS

| | | |
|---|---|---|
| 5,534,609 A | 7/1996 | Lewis et al. |
| 6,074,421 A | 6/2000 | Murphy |
| 6,099,565 A | 8/2000 | Sakura |
| 6,409,954 B1 * | 6/2002 | Mulligan ............... B29C 41/04 264/255 |
| 6,602,452 B2 | 8/2003 | Schuessler |
| 6,605,116 B2 | 8/2003 | Falcon et al. |
| 7,165,964 B2 * | 1/2007 | Schuessler ....... A61B 17/12099 425/429 |
| 2002/0143396 A1 * | 10/2002 | Falcon ..................... A61F 2/12 623/8 |
| 2003/0149481 A1 | 8/2003 | Guest et al. |
| 2003/0163197 A1 | 8/2003 | Chen |
| 2005/0149186 A1 | 7/2005 | Roballey et al. |
| 2007/0135916 A1 | 6/2007 | Maxwell et al. |
| 2008/0221678 A1 | 9/2008 | Hamas |
| 2008/0221679 A1 | 9/2008 | Hamas |
| 2009/0030515 A1 | 1/2009 | Schuessler et al. |
| 2010/0049317 A1 | 2/2010 | Schuessler |
| 2010/0234874 A1 | 9/2010 | Burton |

* cited by examiner

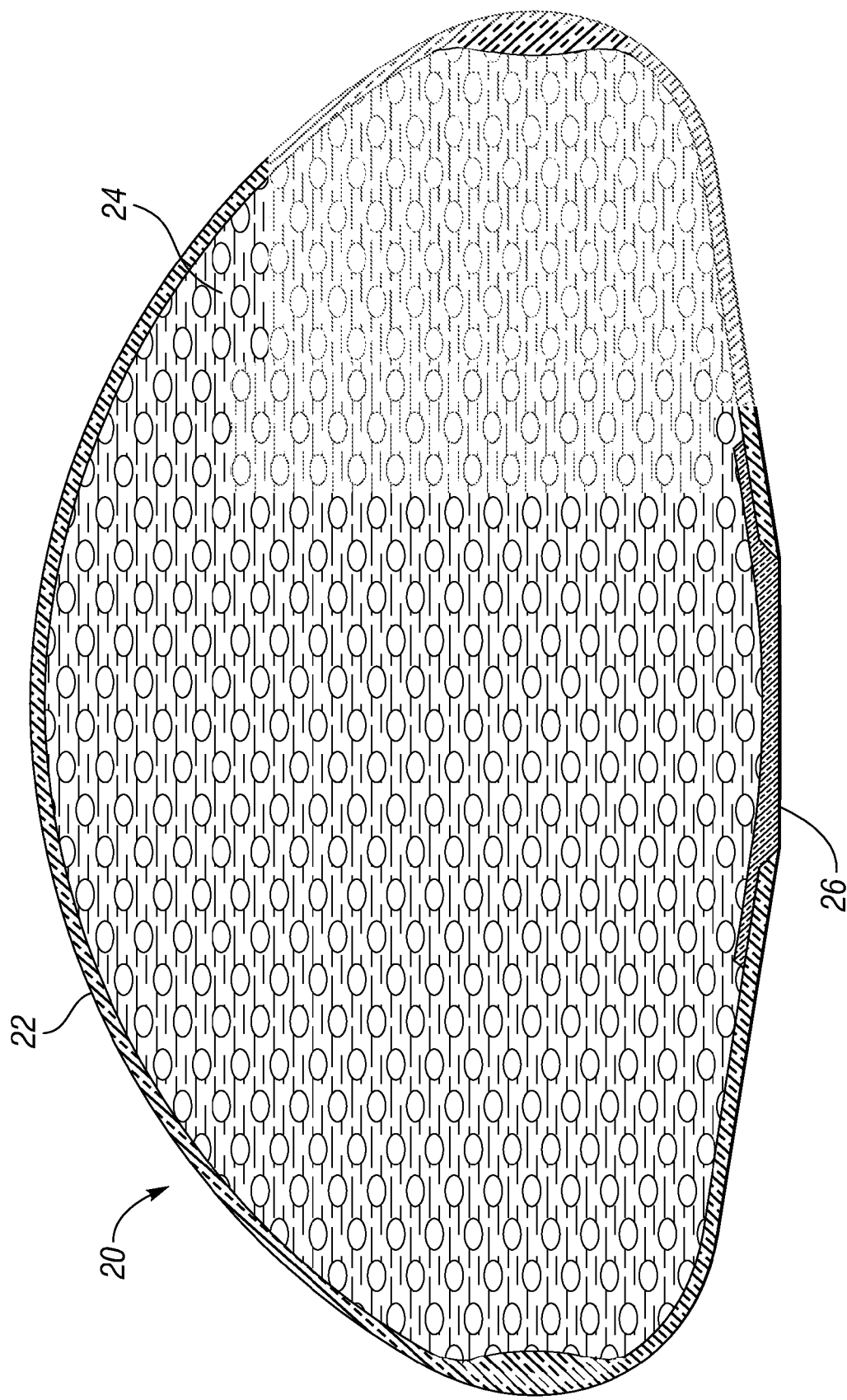

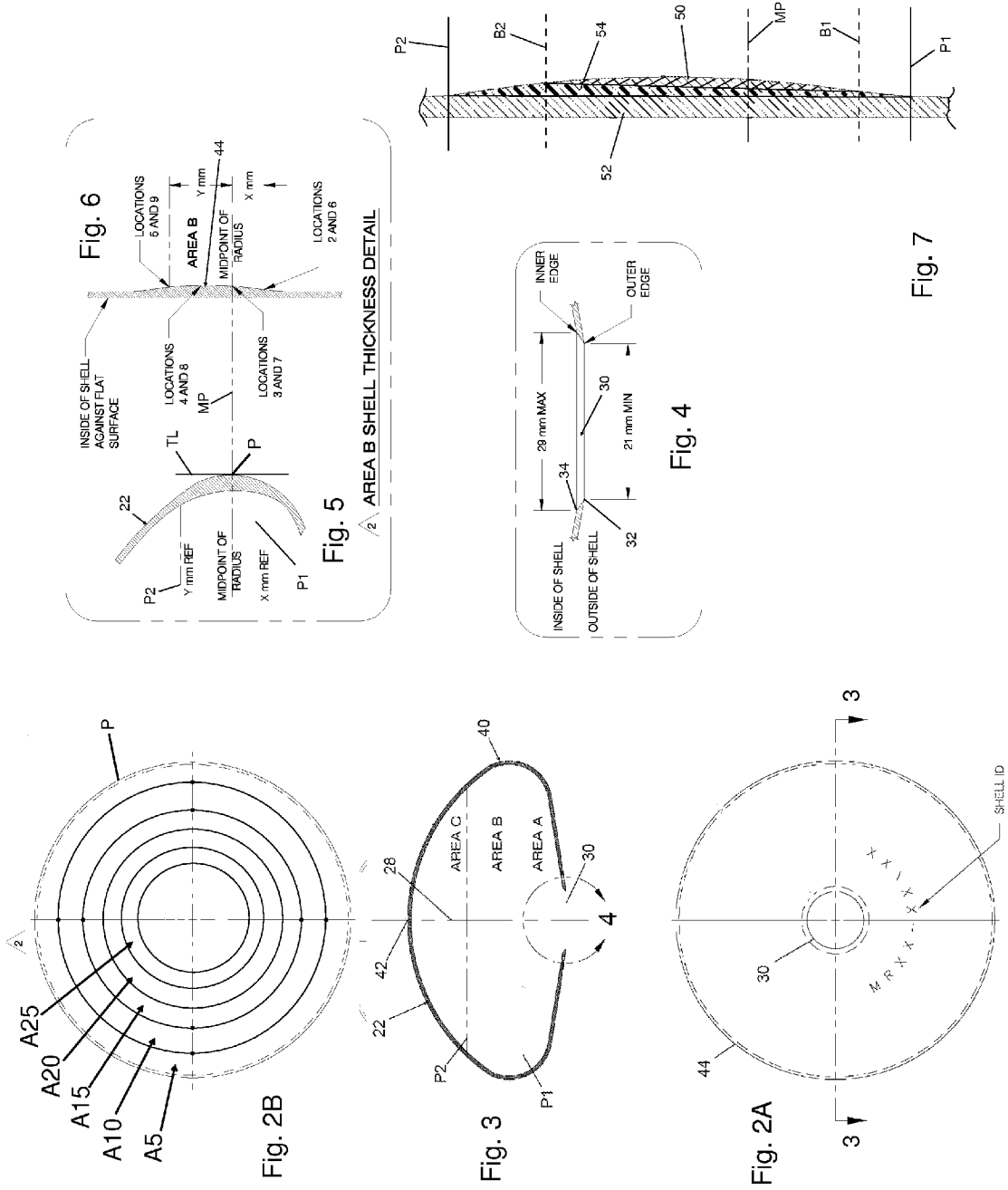

METHOD OF MAKING A REINFORCED PROSTHETIC IMPLANT WITH FLEXIBLE SHELL

RELATED APPLICATION

This application is a divisional of U.S. patent application Ser. No. 12/853,003, filed Aug. 9, 2010, which claims the benefit of U.S. Provisional Patent Application No. 61/234,751, filed on Aug. 18, 2009, the entire disclosure of each of which is incorporated herein by this specific reference.

FIELD OF THE INVENTION

The present invention relates to soft, fluid-filled prosthetic implants and, more particularly, to a fluid-filled prosthetic implant with a reinforced shell.

BACKGROUND OF THE INVENTION

Implantable prostheses are commonly used to replace or augment body tissue. In the case of breast cancer, it is sometimes necessary to remove some or all of the mammary gland and surrounding tissue that creates a void that can be filled with an implantable prosthesis. The implant serves to support surrounding tissue and to maintain the appearance of the body. The restoration of the normal appearance of the body has an extremely beneficial psychological effect on post-operative patients, eliminating much of the shock and depression that often follows extensive surgical procedures. Implantable prostheses are also used more generally for restoring the normal appearance of soft tissue in various areas of the body, such as the buttocks, chin, calf, etc.

Soft implantable prostheses typically include a relatively thin and quite flexible envelope or shell made of vulcanized (cured) silicone elastomer. The shell is filled either with a fluid such as a silicone gel or a normal saline solution. Filling of the shell takes place before or after the shell is inserted through an incision. The present invention pertains to any type of fluid-filled prosthesis, but is especially beneficial for use with gel-filled shells.

Gel-filled breast implants have been in use for over 40 years. In the 1960s, the implants were filled with a relatively thick, viscous silicone gel which created a somewhat non-responsive, unnatural feel. The implants were mostly shaped. During the 1970s and into the 1980s, a softer, more responsive silicone gel was introduced. Some implants included two lumens. Since the 1980s up to the present, improvements to the silicone gel rendered them somewhat more cohesive and firm without being non-responsive.

Confidence in silicone-gel implants ebbed at one stage, as the U.S. Food and Drug Administration had restricted the use of silicone gel-filled implants in the U.S. from 1992 through late 2006 over the concern that silicone gel leaking into the body could be harmful. Since 1992 there have been only two U S manufacturers of gel-filled breast implants, Inamed Corp. (now part of Allergan, Inc. of Irvine, Calif.) and Mentor Corp. (now part of Ethicon/Johnson & Johnson, New Brunswick, N.J.).

Besides safety, another important goal is maintaining breast shape after surgical implantation. During post-operative follow-up—once healing has progressed—surgeons sometimes observe undesirable alterations in the patient's breast shape, specifically signs of skin and/or soft tissue deformation, commonly known to those skilled in the art as wrinkling, knuckling or scalloping. These adverse effects usually occur at the upper or lower pole of the prostheses, along the perimeter of the prosthesis shell or at the base, i.e. the inferior portion closest to the inframammary fold, and become more evident when the recipient changes her anatomical position. Moreover, with the patient in an upright position, these unstable prostheses have been known to collapse or fold in the upper pole and knuckle in the lower pole, further increasing risk of deformed breast shape. Medical prostheses have been proposed in an attempt to eliminate these clinical problems, such as thickened perimeter areas as in U.S. Pat. No. 6,605,116 to Falcon, et al. Indeed, some current breast implant shells feature a nominal increase in wall thickness at the perimeter region, where the radius is the smallest, but adverse alterations in breast shape from folding and such continue to be seen.

Despite attempts to eliminate cosmetic flaws in implanted breast implants, there remains a need for an implant that more reliably retains a natural shape.

BRIEF DESCRIPTION OF THE DRAWINGS

Features and advantages of the present invention will become appreciated as the same become better understood with reference to the specification, claims, and appended drawings wherein:

FIG. 1 is a cross-sectional view through a soft, fluid-filled prosthetic implant having an increased density shell and showing etched information on an exterior label.

FIG. 2A is a rear or posterior plan view of a soft, fluid-filled prosthetic implant shell;

FIG. 2B is a front or anterior plan view of the implant shell of FIG. 2A illustrating a series of drawn concentric bands useful for determining wall thickness across the anterior face;

FIG. 3 is a cross-sectional view through the reinforced shell of FIG. 2A showing a reinforced perimeter area;

FIG. 4 is a detailed cross-sectional view of a fill opening in the shell prior to application of a patch;

FIG. 5 is a detailed cross-sectional view of the reinforced perimeter area B from FIG. 3; and FIG. 6 is a cross-sectional view of the reinforced perimeter area of FIG. 5 shown flattened; and FIG. 7 is an enlarged portion of FIG. 6 illustrating different thickness layers of the reinforced shell.

DETAILED DESCRIPTION

The present application provides a reinforced prosthetic implant shell. The shell is soft and flexible, and includes a fluid filling of either silicone gel or saline to form a soft prosthetic implant. The most common type of soft prosthesis shown for illustration purposes is for breast reconstruction or augmentation, though prostheses formed in accordance with the teachings herein may be used to restore or augment the appearance of soft tissue in the buttocks, chin, calf, etc.

FIG. 1 illustrates an exemplary reinforced breast implant 20 having a flexible outer shell 22 and a fluid 24 filling an internal cavity. In this embodiment, a flush patch 26 covers a manufacturing hole, though other configurations such as a fluid-adjustment valve or other patch may be substituted. The fluid 24 may be a gel, such as a silicone gel, saline, or other suitable fluid filler.

The breast implant 20 may be reinforced in a number of ways, the goal being a stronger implant that resists rupture, while also being more cosmetically acceptable. Specifically, the implants disclosed herein are designed to be 20% more rupture-resistant than previous shells of this type, as measured by an ISO static rupture test. Furthermore, the shells have been tested to be 20% stronger than prior shells based on the major shell strength parameters of break force, tear strength and elongation. At the same time, the shells are about 20% softer from durometer testing, and have about a 50% reduction in gel permeability according to the ASTM silicone disk method. These are performance values based on an Allergan brand Style 15 shell having a volume size of 304 cc, though the results are considered representative for shells of similar styles and sizes. Further details on the specific tests used will be given below.

As will be explained below, the implants may be reinforced generally using several methods: reinforcement of the shell wall, non-homogeneous gel-filling, or both. There are a number of ways disclosed to reinforce the shell wall, and also to selectively fill certain areas with different gels, and it should be understood that the application contemplates the combination of any of these possibilities.

One way to reinforce the fluid-filled, flexible shell implants is to build up shell wall material in strategic areas, whereas most current shells are formed with a uniform wall thickness. More specifically for breast implants, the shells are formed of silicone and have a generally rounded frontal elevational shape with an oval- or teardrop-shaped (hereinafter, "generally oval") central vertical cross-section. The shells have an anterior or first face opposed to a posterior or second face separated by a perimeter line. The radius of curvature of the shell as seen in vertical section is smallest at the perimeter line.

It should be noted that the shells may have either a smooth or textured outer shell. The shell can be circular, oval, crescent-shaped or other suitable shapes. It can be formed of silicone rubber, a laminate of various forms of silicone, silicone copolymers, polyurethane, and various other elastomers in various combinations.

The reinforced shells disclosed herein can have an all barrier shell with a reinforced (RF) perimeter to produce, e.g., round gel-filled breast implants with, e.g., a smooth but matte finish exterior surface. This compares with existing smooth round breast implants currently on the market which have the gel-diffusion inhibiting barrier layer sandwiched between standard silicone layers that comprise the shell and have a glossy exterior surface finish. The shell may be filled with either responsive gel (Allergan TruForm I) or so-called, "Soft Touch" gel (Allergan TruForm II). The shells can be silicone gel-filled, packaged and sterilized ready for physician use. A manufacturing method can be a rotational casting process. This process includes making the shell in two castings. One is a regular casting of a whole shell and the other is for the reinforcement of the shell perimeter only with extra silicone to make it stronger. The rotational shell making process and equipment to be utilized in producing the reinforced shells are disclosed in U.S. Pat. Nos. 6,602,452 and 7,165,964. Additionally, U.S. Patent Publication No. 2009-0030515 having priority date of Jul. 27, 2007 discloses a single layer all barrier material shell.

The shells disclosed herein may be reinforced by adding silicone material around the perimeter region relative to the first or second faces. In general, at least a portion of the perimeter region has a shell wall thickness greater than the average shell wall thickness of either the anterior face or the posterior face. The added material at the perimeter region strengthens that area in which a large percentage of implant ruptures occur. The reinforced perimeter also may help prevent the implant from collapsing or folding, thereby reducing the possibility of undesirable rippling or wrinkling visible through the patient's skin. The remainder of the shell will desirably have a nominal wall thickness to retain the overall softness and supple feel of the implant.

FIG. 2A is a rear or posterior plan view of the soft prosthetic implant shell 22, while FIG. 3 is a horizontal cross-section through the shell with the posterior face down and the anterior face up. In this embodiment, the shell 22 is axi-symmetric about central axis 28, so the vertical cross-section will be the same. In other embodiments, the shell 22 may have a contour, similar to a teardrop in side profile, with a larger lower lobe and thinner upper portion. Those of skill in the art will recognize that the particular wall thickening described for the axi-symmetric shell shown may be applied to a non axi-symmetric shell, or the increased wall thickness may be non-uniform around the shell perimeter as needed.

FIGS. 2A and 3 show the manufacturing hole 30 of the shell 22, without the flush patch 26 described above. As shown in the detailed view of FIG. 4, the manufacturing hole 30 defines a beveled edge with a smaller outer rim 32 opening to a larger inner rim 34. This shape helps mate with the flush patch 26 for a smoother final assembly.

FIG. 5 is a detailed cross-sectional view of the reinforced perimeter 40 from area B shown in FIG. 3, and FIG. 6 is the same region shown flattened. The shell 22 may be segregated into three discrete geometric bands or areas, A, B and C, perpendicular to the central axis 28 as seen in FIG. 3. Area A comprises a posterior band, area B a middle band, and area C an anterior band.

A detailed understanding of the shell geometry is necessary to specify particular thicknesses/ranges. The shell 22 as seen in cross-section in FIG. 3 extends from the lower manufacturing hole 30 to an upper apex 42 (in this embodiment, the uppermost point on the anterior face). The shell 22 is outwardly convex in this view, and has a maximum radius about the central axis 28 along a radius midpoint plane MP at a perimeter P, as seen in FIGS. 5 and 6. The radius midpoint plane MP includes the perimeter P or generatrix at which a line TL tangent to the exterior curvature of the shell 22 parallels the central axis 28. The perimeter P (or radius) of the shell thus defines the widest radial plane, and forms a line around the shell at the outermost diameter of the device as it sits posterior side down on a flat surface. This perimeter line separates the anterior face from the posterior face. FIG. 2B shows the anterior face circumscribed by the perimeter P.

To be clear, the anterior face is the top portion of the shell (with the apex 42 as its center) extending down to the extreme outer edge or perimeter line P, while the posterior face extends around the bottom portion of the shell below the perimeter line. A perimeter region can be defined as a region (as opposed to a line) where the anterior face and posterior face meet and containing portions of both the anterior face and the posterior face. The present invention provides a reinforced or thickened wall portion in the perimeter region with a longitudinal axis coincident with the central axis 28 of the perimeter P.

To define the perimeter region, certain areas may be delineated on the shell. Posterior area A extends from the manufacturing hole 30 to a first lateral plane P1 spaced X mm axially below or in the posterior direction from the radius midpoint plane MP. Anterior area C extends from the shell apex 42 to a second lateral plane P2 spaced Y mm axially above or in the anterior direction from the radius midpoint plane MP. Finally, middle area B extends between areas A and C. In a preferred configuration, the distance X ranges between about 2-6 mm, and the distance Y ranges between about 7-20 mm. For instance, the distance X is about 5 mm and the distance Y is about 10 mm.

The increased thickness of the wall of the shell 22 is seen in the details of FIGS. 5 and 6, and may be described relative to the areas A, B, and C. In an exemplary embodiment, the wall thickness in posterior area A is between about 0.013-0.040 in (0.33-1.02 mm), as measured at points spaced about 3-5 mm from the inner edge of the shell hole 30. The wall thickness in middle or reinforced area B is between about 0.020-0.060 in (0.51-1.52 mm), as measured at various points from first lateral plane P1 to the second lateral plane P2. Finally, the wall thickness in anterior area C is between about 0.013-0.040 in (0.33-1.02 mm), as measured at points located from about halfway between the midpoint plane MP and the apex 42 to within about 15 mm of the apex.

The nominal (non-reinforced) shell wall thickness is at least 0.254 mm (0.010 inches), and desirably about 0.456 mm (0.018 inches). The implant shell may be made by dip-forming, spray-forming, or rotational molding. The exterior may be smooth or textured.

FIG. 6 shows that a point of maximum thickness 44 desirably exists just above, or in the anterior direction, from the midpoint plane MP. In one exemplary form, the wall thickness gradually increases from both the first and second lateral planes P1, P2 toward the midpoint plane MP. Preferably, the linear distance (X+Y) between the first and second lateral planes P1, P2 is between about 15-17 mm, and potentially up to about 24 mm. In one embodiment, the thickness increases symmetrically therebetween so that the point of maximum thickness 44 is equidistant from either lateral plane. In other words, the central portion of the region of increased thickness is offset in an anterior direction from the midpoint plane MP. Of course, other configurations are possible.

It should be noted that the region of increased thickness may extend outside of the middle area B into areas A or C, as is shown in FIG. 6. Other configurations are contemplated, and the placement of the region of increased thickness as well as the point of maximum thickness 44 may be altered depending on the size or shape of the particular shell, the shell material, the nominal thickness of the shell in the other areas, and other factors. It should also be noted that though the region of increased thickness desirably circumscribes the perimeter evenly, it may vary around the shell, and may even be omitted in some areas.

FIG. 7 is an enlarged portion of FIG. 6 illustrating different thickness layers of the reinforced shell. It is important to recognize that not all of the increased thickness in the perimeter region of the shell is deliberately formed, and some occurs as a normal consequence of the preferred rotational molding process.

The reinforced shell is desirably made by rotational molding (as opposed to mandrel dipping). In particular, the implant shells of the present invention are desirably formed using a rotational molding system, such as disclosed in U.S. Pat. Nos. 6,602,452 and 7,165,964, and U.S. Patent Publication No 2008-0181981, all to Schuessler, which are expressly incorporated herein by this reference. Schuessler discloses a rotational molding machine for forming medical articles, in particular for molding silicone elastomer shells for breast implants.

One method of making the reinforced shell comprises introducing a small amount of liquid silicone in a rotational mold cavity and rotating the mold about only one axis (typically while heating). This creates a band of silicone within the mold around the perimeter location. Next more (or most) of the liquid silicone is added into the mold cavity and the mold is then rotated about two or more axes (and also typically while heating) to thereby form the entire shell—now with a reinforced perimeter band going all the way around the shell.

The molded shell is then cured, either before or with the application of a patch over the mold hole. A silicone gel is then injected into the shell interior.

Three thickness layers are illustrated in FIGS. 7, though it should be understood that the wall of the shell 22 may be homogenous in composition, with the three layers merely representing areas where material deposits during the mold process. Specifically, a first or outer layer 50 represents a first amount of shell wall material formed into a peripheral band. A second or inner layer 52 and a third, intermediate layer 54, represents a second amount of shell wall material forming the majority of the shell 22. That is, the preferred process for forming the shell 22 comprises first rotational casting the peripheral band 50 around a mold cavity perimeter region, and then casting the entire shell including simultaneously casting the second and third layers 52, 54 within the peripheral band.

The peripheral band 50 extends an axial distance (when flattened) between posterior and anterior borders B1, B2. As mentioned above, the distance between the first and second lateral planes P1, P2 is between about 15-17 mm, and potentially up to 24 mm. However, the axial distance between the posterior and anterior borders B1, B2 of the peripheral band 50 is less than that, and preferably ranges between about 10-20 mm. The rest of the thickened shell wall, represented by the intermediate layer 54, is a consequence of the rotational molding process and is formed in all shells made in this manner. Stated another way, only the first or outer layer 50 comprises material added to a conventional rotationally molded shell. This also means that the region of increased thickness that extends between the first and second lateral planes P1, P2 is not entirely a "reinforced portion," in that the intermediate layer 54 is present in prior shells. The reader will understand that illustration of the intermediate layer 54 is for convenience and comparison with the other two layers 50, 52, though the second casting of silicone material will build up smoothly against the interior of the mold cavity and preformed peripheral band 50. Therefore, the extra material that accumulates in the peripheral region cannot be pinpointed to the inside or outside of that casting, and the depiction of the intermediate layer 54 on the outside is arbitrary in that respect.

To define the reinforced portion more precisely, it is limited to the area of the shell that is less than about 0.5 inches (about 12.7 mm) from the perimeter (line at the midplane MP). A methodology of measuring this thickness and assessing shells is important to be able to quantify where the reinforced area actually starts.

By definition a reinforced region will be thicker than other regions, and the thickness of any one region will be determined as an average. It will be understood that, as a practical matter, only a limited number of single point measurements may be made to determine the average thickness of any one region of the implant. One method used herein is to divide the shell anterior face into concentric bands centered on the central axis 28, determine the average thickness of each band, determine the proportion of each band relative to the total anterior face surface area, and then arrive at a total average thickness for the whole anterior face as well as the reinforced region.

First shell thickness measurements are taken from the perimeter P and every 5 mm along a line (termed a spline) on the shell surface to the apex 42. Repeat at 90 degree intervals around the shell for a total of 4 splines or sets of thickness measurements. Each 5 mm interval along the splines then determines a band A5, A10, etc. (FIG. 2B) which in turn locates eight thickness measurements around its borders. For instance, FIG. 2B shows eight dots located at the eight spline corners for the second largest band A10, which is between 5-10 mm onto the anterior face from the perimeter P. Thickness measurements at these eight points are taken and their average is then an approximation of the average thickness of the thickness of whole band A10.

The contribution of each band (A5, A10, etc.) to the total area of the anterior face depends on the size or diameter of the shell 22 which will determine the area of each band. Given a certain shell diameter, and assuming the anterior shell surface is flat, a weighted average calculation for each band's contribution to the whole shell can be done. Exemplary shell surface area calculations are shown in the table below for a shell having a diameter of 100 mm.

TABLE I

| Band ID | Outer Radius (OR) mm | Inner Radius (IR) mm | Area of Band (mm$^2$) = $\pi(OR)^2 - \pi(IR)^2$ | Weighted Avg Area of Band |
|---|---|---|---|---|
| A5 | 50 | 45 | 1492 | 19.0% |
| A10 | 45 | 40 | 1335 | 17.0% |
| A15 | 40 | 35 | 1178 | 15.0% |
| A20 | 35 | 30 | 1021 | 13.0% |
| A25 | 30 | 25 | 864 | 11.0% |
| A30 | 25 | 20 | 707 | 9.0% |
| A35 | 20 | 15 | 550 | 7.0% |
| A40 | 15 | 10 | 393 | 5.0% |
| A45 | 10 | 5 | 236 | 3.0% |
| A50 | 5 | 0 | 79 | 1.0% |
| Total Area of Anterior Face | | | 7854 | 100% |

With the relative band areas defined, measurement of band shell thickness enables an Anterior Face Average Thickness to be calculated. Several ways to measure thickness are contemplated, including a non-destructive method that produced exemplary data as follows:

TABLE II

| Band ID | Band Average Thickness = Avg of two borders (8 total points) mm | Weighted Avg Area of Band | Weighted Component of Band Avg Thickness, mm |
|---|---|---|---|
| A5 | 0.0348 | 19.0% | 0.0066 |
| A10 | 0.0244 | 17.0% | 0.0041 |
| A15 | 0.0214 | 15.0% | 0.0032 |
| A20 | 0.0228 | 13.0% | 0.0030 |
| A25 | 0.0235 | 11.0% | 0.0026 |
| A30 | 0.0223 | 9.0% | 0.0020 |
| A35 | 0.0213 | 7.0% | 0.0015 |
| A40 | 0.0206 | 5.0% | 0.0010 |
| A45 | 0.0203 | 3.0% | 0.0006 |
| A50 | 0.0199 | 1.0% | 0.0002 |
| Total Weighted Anterior Face Average Thickness | | | 0.0248 |

The present application desirably provides shells 22 in which bands A5 and A10 are reinforced, or have a thickness greater than the average anterior thickness, and the bands farther than 10 mm away from the perimeter P (i.e., A15, A20, etc.) have an average thickness less than the average anterior thickness, and are thus not part of the reinforced region. Stated another way, the reinforced perimetric region does not extend farther than 10 mm from the perimeter line P onto the anterior face. Alternatively, a larger reinforced region may be provided, such as one which extends at least 50 mm from the perimetric line P, or substantially the entire anterior face. These exemplary dimensions for the reinforced region may be mirrored onto the posterior face, or may be limited only to the anterior face.

Another more accurate measurement technique includes destruction of a sample of shells and more data points. For instance, the measured band increments will be approximately every 0.050 inches, or approximately 1 mm instead of 5 mm. Also, the number of splines will be increased from four to eight, or about every 45° around the shell. One useful method is to sample more shells using the non-destructive fewer-point measurement model as a screening tool. Once sufficient data is gathered, a correlation study may be perfomed between the original non-destructive tests and the finer destructive model to validate the non-destructive model.

As mentioned above, a preferred rotational molding techniques results in a relatively smooth transition between the perimetric reinforced region and the anterior and posterior faces. However, other configurations are possible, which can be obtained via rotational molding or other formation techniques. For instance, the transition between the posterior and anterior faces may not be smooth, or the transition between the reinforced perimeter and just the anterior face may not be smooth. One example of a non-smooth transition is a step between the regions which may be formed by placing an insert into the rotational mold. Or, the mold itself may be provided with a corner or other such discontinuity to result in a step or corner on the exterior of the shell.

Prototypes of the reinforced shells have been made with rotational molding with different levels of silicone material in the preferred two step casting process; a first casting step to create a band of silicone within the mold around the perimeter, and a second casting step to form the entire shell. To better determine the proper fill amounts, 76 different breast implant shells were formed from 76 different silicone first and second dispersion fills, consisting of five separate series of castings of different profiles over a range of mold sizes, tabulated below. The mold diameters ranged from 9.0 to 17.5 cm, though not all the test series included all of the diameters.

One example of the two-step casting process as detailed in the first row in Table III below (mold #1090) includes a first casting of 4.6 g of 36.3% solid silicone/xylene dispersion. The operator introduces the first casting material into the rotational casting mold and spins the mold about its central axis so that the first casting material accumulates around the perimeter. The operator then introduces 24.7 g of the second casting material (36.3% dispersion) into the mold and spins the mold about multiple axes so that the second casting material substantially evenly covers the inside of the mold and the band of first casting material. Both casting steps are desirably done in conjunction with heating and solvent gasses are vented throughout. The first casting may or may not be cured prior to performance of the second casting.

TABLE III

| Mold # | Mold dia. (cm) | Single cast target - 35% solid (g) | 1$^{st}$ Cast - 36.3% solid (g) | 2$^{nd}$ Cast - 36.3% solid (g) | 1$^{st}$ Cast % |
|---|---|---|---|---|---|
| 1090 | 9.0 | 22.4 | 4.6 | 24.7 | 15.7 |
| 1095 | 9.5 | 24.8 | 5.0 | 27.4 | 15.4 |
| 1100 | 10.0 | 27.4 | 5.4 | 30.2 | 15.2 |

TABLE III-continued

| Mold # | Mold dia. (cm) | Single cast target - 35% solid (g) | 1st Cast - 36.3% solid (g) | 2nd Cast - 36.3% solid (g) | 1st Cast % |
|---|---|---|---|---|---|
| 1105 | 10.5 | 30.1 | 5.9 | 33.2 | 15.1 |
| 1110 | 11.0 | 32.9 | 6.4 | 36.4 | 15.0 |
| 1115 | 11.5 | 36.0 | 6.8 | 39.8 | 14.6 |
| 1120 | 12.0 | 39.2 | 7.4 | 43.3 | 14.6 |
| 1125 | 12.5 | 42.6 | 7.9 | 47.0 | 14.4 |
| 1130 | 13.0 | 46.0 | 8.4 | 50.8 | 14.2 |
| 1135 | 13.5 | 49.6 | 9.0 | 54.8 | 14.1 |
| 1140 | 14.0 | 53.4 | 9.6 | 59.0 | 14.0 |
| 1145 | 14.5 | 57.3 | 10.2 | 63.2 | 13.9 |
| 1150 | 15.0 | 61.3 | 10.8 | 67.7 | 13.8 |
| 1155 | 15.5 | 65.5 | 11.4 | 72.3 | 13.6 |
| 1160 | 16.0 | 69.8 | 12.1 | 77.0 | 13.6 |
| 1165 | 16.5 | 74.2 | 12.8 | 81.9 | 13.5 |
| 1170 | 17.0 | 78.8 | 13.5 | 87.0 | 13.4 |
| 1175 | 17.5 | 83.5 | 14.2 | 92.1 | 13.4 |

TABLE IV

| Mold # | Mold dia. (cm) | Single cast target - 35% solid (g) | 1st Cast - 36.3% solid (g) | 2nd Cast - 36.3% solid (g) | 1st Cast % |
|---|---|---|---|---|---|
| 2090 | 9.0 | 22.8 | 5.5 | 25.2 | 17.9 |
| 2095 | 9.5 | 25.4 | 6.0 | 28.0 | 17.6 |
| 2100 | 10.0 | 28.0 | 6.6 | 30.9 | 17.6 |
| 2105 | 10.5 | 30.8 | 7.1 | 34.0 | 17.3 |
| 2110 | 11.0 | 33.7 | 7.7 | 37.2 | 17.1 |
| 2115 | 11.5 | 36.8 | 8.3 | 40.7 | 16.9 |
| 2120 | 12.0 | 40.1 | 8.9 | 44.3 | 16.7 |
| 2125 | 12.5 | 43.5 | 9.6 | 48.0 | 16.7 |
| 2130 | 13.0 | 47.1 | 10.2 | 52.0 | 16.4 |
| 2135 | 13.5 | 50.8 | 10.9 | 56.1 | 16.3 |
| 2140 | 14.0 | 54.6 | 11.6 | 60.3 | 16.1 |
| 2145 | 14.5 | 58.6 | 12.4 | 64.7 | 16.1 |
| 2150 | 15.0 | 62.7 | 13.1 | 69.2 | 15.9 |
| 2155 | 15.5 | 66.9 | 13.9 | 73.9 | 15.7 |
| 2160 | 16.0 | 71.3 | 14.7 | 78.8 | 15.7 |
| 2165 | 16.5 | 75.9 | 15.5 | 83.8 | 15.6 |
| 2170 | 17.0 | 80.5 | 16.4 | 88.9 | 15.6 |

TABLE V

| Mold # | Mold dia. (cm) | Single cast target - 35% solid (g) | 1st Cast - 36.3% solid (g) | 2nd Cast - 36.3% solid (g) | 1st Cast % |
|---|---|---|---|---|---|
| 3090 | 9.0 | 23.6 | 6.5 | 26.0 | 20.0 |
| 3095 | 9.5 | 26.2 | 7.1 | 28.9 | 19.7 |
| 3100 | 10.0 | 28.9 | 7.7 | 32.0 | 19.4 |
| 3105 | 10.5 | 31.8 | 8.4 | 35.1 | 19.3 |
| 3110 | 11.0 | 34.9 | 9.1 | 38.5 | 19.2 |
| 3115 | 11.5 | 38.1 | 9.8 | 42.0 | 18.9 |
| 3120 | 12.0 | 41.5 | 10.5 | 45.8 | 18.7 |
| 3125 | 12.5 | 45.0 | 11.3 | 49.7 | 18.5 |
| 3130 | 13.0 | 48.7 | 12.1 | 53.7 | 18.4 |
| 3135 | 13.5 | 52.5 | 12.9 | 57.9 | 18.2 |
| 3140 | 14.0 | 56.4 | 13.7 | 62.3 | 18.0 |
| 3145 | 14.5 | 60.6 | 14.6 | 66.9 | 17.9 |
| 3150 | 15.0 | 64.8 | 15.4 | 71.5 | 17.7 |
| 3155 | 15.5 | 69.2 | 16.4 | 76.4 | 17.7 |
| 3160 | 16.0 | 73.7 | 17.3 | 81.4 | 17.5 |

TABLE VI

| Mold # | Mold dia. (cm) | Single cast target - 35% solid (g) | 1st Cast - 36.3% solid (g) | 2nd Cast - 36.3% solid (g) | 1st Cast % |
|---|---|---|---|---|---|
| 4090 | 9.0 | 24.6 | 7.5 | 27.1 | 21.7 |
| 4095 | 9.5 | 27.3 | 8.2 | 30.1 | 21.4 |
| 4100 | 10.0 | 30.2 | 8.9 | 33.3 | 21.1 |
| 4105 | 10.5 | 33.2 | 9.7 | 36.7 | 20.9 |
| 4110 | 11.0 | 36.4 | 10.4 | 40.2 | 20.6 |
| 4115 | 11.5 | 39.7 | 11.3 | 43.9 | 20.5 |
| 4120 | 12.0 | 43.3 | 12.1 | 47.8 | 20.2 |
| 4125 | 12.5 | 46.9 | 13.0 | 51.8 | 20.1 |
| 4130 | 13.0 | 50.8 | 13.9 | 56.0 | 19.9 |
| 4135 | 13.5 | 54.8 | 14.8 | 60.4 | 19.7 |
| 4140 | 14.0 | 58.9 | 15.8 | 65.0 | 19.5 |
| 4145 | 14.5 | 63.2 | 16.7 | 69.7 | 19.3 |
| 4150 | 15.0 | 67.6 | 17.8 | 74.6 | 19.3 |
| 4155 | 15.5 | 72.2 | 18.8 | 79.8 | 19.1 |

TABLE VII

| Mold # | Mold dia. (cm) | Single cast target - 35% solid (g) | 1st Cast - 36.3% solid (g) | 2nd Cast - 36.3% solid (g) | 1st Cast % |
|---|---|---|---|---|---|
| 5090 | 9.0 | 27.1 | 8.5 | 29.9 | 22.1 |
| 5095 | 9.5 | 30.1 | 9.2 | 33.3 | 21.9 |
| 5100 | 10.0 | 33.3 | 10.1 | 36.8 | 21.5 |
| 5105 | 10.5 | 36.7 | 10.9 | 40.5 | 21.2 |
| 5110 | 11.0 | 40.2 | 11.8 | 44.4 | 21.0 |
| 5115 | 11.5 | 43.9 | 12.7 | 48.4 | 20.8 |
| 5120 | 12.0 | 47.8 | 13.7 | 52.7 | 20.6 |
| 5125 | 12.5 | 51.8 | 14.7 | 57.2 | 20.4 |
| 5130 | 13.0 | 56.1 | 15.7 | 61.9 | 20.2 |
| 5135 | 13.5 | 60.5 | 16.7 | 66.8 | 20.0 |
| 5140 | 14.0 | 65.0 | 17.8 | 71.8 | 19.9 |
| 5145 | 14.5 | 69.8 | 18.9 | 77.0 | 19.7 |

These masses of first and second dispersion fills presume a silicone dispersion having 36.3% solids. That is, the dispersion includes 36.3% by mass solid silicone particles and the rest a solvent, typically xylene. If the dispersion varies, the amounts for the first and second castings will also vary to ensure formation of the same thickness shell wall. The five tables show preferred results for the different mold profiles over a range of diameters. That is, a conventional shell is typically formed with a single dispersion fill the amount of which is shown in column 3 It should be noted that the dispersion for the target single casting is slightly different, 35% rather than 36.3%.

The last column indicates the ratio in percent of the first reinforcement cast to the second shell cast. Several trends are seen. First, the percent of first-to-second castings decreases as the mold size increases. This is because the surface area of the entire mold cavity increases at a greater rate than the perimeter region with increasing diameter, and thus proportionally more of the second cast will be required. Secondly, as the target single cast amount increases, from Table III to Table VII, the percent of the first reinforcement cast increases for any particular mold diameter. Finally, the amount of silicone dispersion used in the first perimeter cast is between about 13-23% in all of the examples, with the caveat that the range may change with a different solid percent dispersion.

The reinforced prosthetic implant may also be characterized by alterations in gel filler cohesiveness. Implants having fillers of varying density are known in the art. For example, Allergan's Style 510 Dual Gel breast implant contains two different cohesive gels. The posterior of the implant is made from standard cohesive gel, while the anterior is made from a high cohesive gel. This configuration provides superior projection and support, emphasizing the nipple/areola area of the implant.

U.S. Patent Publication No. 2007-0135916 to Maxwell, filed Oct. 25, 2006 is expressly incorporated herein by this reference.

In addition to reinforcing the perimeter region, therefore, one alternative to make the implant is to cast a ring of soft gel (less cohesive) under the radially reinforced area so that the feel of that area is more cosmetically acceptable. The soft filler counterbalances the relatively more rigid perimeter area. The remainder of the shell is filled with a firmer gel (more cohesive) that will more effectively maintain the implant shape than the softer gel.

A further alternative technique to make the implant is to reinforce the radius or perimeter area by using a ring of firmer gel only around the perimeter, which will better resist deformation. The rest of the shell is filled with a softer gel. This technique can be done with or without also reinforcing the shell perimeter.

Another important aspect of the present invention is that the implant desirably utilizes a single layer all barrier shell ("ABS"). In previous implants, the barrier layer was sandwiched between a non-barrier outer layer and a non-barrier inner layer. The ABS layer is made of silicone in which about 15% of the molecules have phenyl substituents. The non-ABS layers have only about 5% phenyl substituents. More particularly, the shell made of a single barrier layer. The barrier layer is formed of a homogeneous silicone elastomer capable of sterically retarding permeation of the silicone gel through the shell and having a bleed rate that is less than about 40% of the bleed rate of current shells which use a sandwiched construction with an internal barrier layer. Further, the barrier layer shell is made of a material that exhibits a wet strength that is comparable to or greater than current shells. The silicone elastomer may be a dimethyl polysiloxane, and the substituted chemical group is a diphenyl group with a minimum mole percent of at least about 10%, for example, at least about 13%. Such materials have been described in Schuessler et al., U.S. Patent Publication No. 2009-0030515, the entire disclosure of which is expressly incorporated herein by this reference.

Compression tests on these reinforced shells are on average about 20% stronger than the non-reinforced shells.

Using state-of-the-art manufacturing technology enables fabrication of a new silicone gel breast implant shell that is stronger and softer than prior shells. The gel fill may be the same as the gel fill currently available today in the U.S. Based on independent lab testing of physical properties, this round, smooth breast implant shell:
  a. Features a shell design with an identifiable reinforced perimeter for 20% higher rupture resistance as measured by ISO static rupture testing. Based on data gathered from explanted breast implants, over half of documented ruptures occur at the perimeter.
  b. Has reduced gel permeability by 50% vs. the leading competitor (Based on test method per ASTM F703: 2007).
  c. Is 20% stronger than the leading competitive shell based on overall average shell strength measures of break force, tear force and elongation (Uses test methods ASTM D412).
  d. Has at least 15% less surface friction than other smooth shells (Based on measure of static coefficient of friction as measured per test method ASTM D1894-06).
  e. Is 20% softer than the leading competitive shell (Based on durometer measurements per ASTM D2240).

A reinforced shell breast implant disclosed herein may be implanted in any number of well-known methods. For instance, a number of possible incisions used by surgeons include an inframammary incision, a periareolar incision, and a transaxillary incision. A resilient sizer may be used to determine the size (and possibly shape) of the appropriate implant, which is then selected and prepared for implant. The surgeon collapses the breast implant, sometimes with the assistance of a tool such as a funnel, and delivers the implant through the chosen incision. Once inserted and oriented properly, the implants resiliently expand back to their original forms without much if any manipulation by the surgeon. At this point, the surgeon can finally observe and evaluate whether the size and shape of the selected implant is appropriate for the patient.

Although the invention has been described and illustrated with a certain degree of particularity, it is understood that the present disclosure has been made only by way of example, and that numerous changes in the combination and arrangement of parts can be resorted to by those skilled in the art without departing from the scope of the invention, as hereinafter claimed.

What is claimed is:

1. A method of making a shell for a gel-filled prosthetic implant, comprising:
  providing a mold having a cavity and defining a generally oval vertical cross-section with a first face opposed to a second face and separated by a perimeter region;
  introducing a silicone elastomer into the mold cavity;
  causing the silicone elastomer to distribute generally evenly around the entire mold cavity;
  curing the silicone elastomer to form a hollow implant shell;
  introducing a first silicone elastomer gel into the hollow implant shell;
  causing the first silicone elastomer gel to distribute generally evenly around a perimeter region of the hollow implant shell;
  allowing the first silicone elastomer gel to coalesce and form a ring within the perimeter region of the hollow implant shell; and
  removing the implant shell from the mold cavity.

2. The method of claim 1, wherein the first silicone elastomer gel has a particular gel cohesiveness, and after the step of allowing the first silicone elastomer gel to coalesce, further including:
  introducing a second silicone elastomer gel into the hollow implant shell, the second silicone elastomer gel having a lower gel cohesiveness than the first silicone elastomer gel.

3. The method of claim 1, wherein the first silicone elastomer gel has a particular gel cohesiveness, and after the step of allowing the first silicone elastomer gel to coalesce, further including:
  introducing a second silicone elastomer gel into the hollow implant shell, the second silicone elastomer gel having a greater gel cohesiveness than the first silicone elastomer gel.

4. The method of claim 1, wherein the mold is part of a rotational casting machine, and the step of causing the first silicone elastomer gel to distribute generally evenly around a perimeter region comprises rotating the mold about only one axis.

* * * * *

UNITED STATES PATENT AND TRADEMARK OFFICE
CERTIFICATE OF CORRECTION

PATENT NO.        : 9,486,308 B2
APPLICATION NO.   : 14/088163
DATED             : November 8, 2016
INVENTOR(S)       : David J. Schuessler et al.

Page 1 of 1

It is certified that error appears in the above-identified patent and that said Letters Patent is hereby corrected as shown below:

On the Title Page

In item (57), in Column 2, in "Abstract", Line 12, after "helps" insert -- to --.

In the Specification

In Column 1, Line 56, delete "U S" and insert -- U.S. --, therefor.

In Column 2, Line 39, after "3;" delete "and".

In Column 7, Line 65, delete "reinformed" and insert -- reinforced --, therefor.

In Column 8, Line 16, delete "perfomed" and insert -- performed --, therefor.

In Column 10, Line 43, delete "3" and insert -- 3. --, therefor.

Signed and Sealed this
Twenty-first Day of March, 2017

Michelle K. Lee
*Director of the United States Patent and Trademark Office*